(12) United States Patent
Kim et al.

(10) Patent No.: US 10,258,310 B2
(45) Date of Patent: Apr. 16, 2019

(54) ULTRASONIC PROBE AND METHOD OF MANUFACTURING THE SAME

(71) Applicant: SAMSUNG ELECTRONICS CO., LTD., Suwon-si (KR)

(72) Inventors: Sung Ki Kim, Seoul (KR); Chang Yeon Won, Seoul (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 846 days.

(21) Appl. No.: 14/613,500

(22) Filed: Feb. 4, 2015

(65) Prior Publication Data

US 2015/0320393 A1 Nov. 12, 2015

(30) Foreign Application Priority Data

May 8, 2014 (KR) .................. 10-2014-0054784

(51) Int. Cl.
*A61B 8/14* (2006.01)
*A61B 8/00* (2006.01)
*G01S 7/52* (2006.01)
*B06B 1/02* (2006.01)
*G01S 15/89* (2006.01)

(52) U.S. Cl.
CPC .......... *A61B 8/4444* (2013.01); *A61B 8/4494* (2013.01); *A61B 8/546* (2013.01); *B06B 1/02* (2013.01); *G01S 7/52079* (2013.01); *G01S 15/8915* (2013.01); *A61B 8/4405* (2013.01); *A61B 2560/06* (2013.01); *Y10T 29/49007* (2015.01)

(58) Field of Classification Search
CPC .............. A61B 2560/06; A61B 8/4405; A61B 8/4444; A61B 8/4494; A61B 8/546; B06B 1/02; G01S 15/8915; G01S 7/52079; Y10T 29/49007
See application file for complete search history.

(56) References Cited

U.S. PATENT DOCUMENTS

| | | | |
|---|---|---|---|
| 2014/0146116 A1* | 5/2014 | Paschkewitz | B41J 2/14233 347/88 |
| 2014/0238640 A1* | 8/2014 | Arvelo | F16L 41/10 165/76 |
| 2015/0011889 A1* | 1/2015 | Lee | A61B 8/4444 600/459 |

FOREIGN PATENT DOCUMENTS

| | | |
|---|---|---|
| JP | 2009-82567 A | 4/2009 |
| JP | 2012-145404 A | 8/2012 |
| KR | 10-2010-0047395 A | 5/2010 |
| KR | 10-2013-0122202 A | 11/2013 |

OTHER PUBLICATIONS

Communication dated Aug. 29, 2016 issued by the Korean Intellectual Property Office in counterpart Korean Patent Application No. 10-2014-0054784.
Communication dated Mar. 14, 2016, issued by the Korean Intellectual Property Office in counterpart Korean Patent Application No. 10-2014-0054784.

* cited by examiner

*Primary Examiner* — Mark Remaly
(74) *Attorney, Agent, or Firm* — Sughrue Mion, PLLC

(57) ABSTRACT

The ultrasonic probe includes a transducer array that generates ultrasonic waves, a backing layer that is provided on a rear surface of the transducer array, a pulsating heat pipe that absorbs heat generated in the transducer array, and a heat radiation unit that receives the heat from the pulsating heat pipe to emit the received heat to the outside.

15 Claims, 17 Drawing Sheets

ULTRASONIC PROBE AND METHOD OF MANUFACTURING THE SAME

CROSS-REFERENCE TO RELATED APPLICATION

This application claims priority from Korean Patent Application No. 10-2014-0054784, filed on May 8, 2014 in the Korean Intellectual Property Office, the disclosure of which is incorporated herein by reference in its entirety.

BACKGROUND

1. Field

Exemplary embodiments relate to an ultrasonic probe that radiates ultrasonic waves onto an object and receives echo ultrasonic waves reflected from the object, and a method of manufacturing the same.

2. Description of the Related Art

An ultrasonic imaging apparatus acquires ultrasonic images of an object by transmitting ultrasonic waves to the object and receiving the reflected ultrasonic waves from the object.

In order to transmit and receive the ultrasonic waves, the ultrasonic imaging apparatus may include an ultrasonic probe. The ultrasonic probe may transmit the ultrasonic waves onto the object through a transducer and receive echo ultrasonic waves reflected from the object.

The transducer may be vibrated by receiving a supply of current, thereby generating ultrasonic waves. In this instance, the vibration of the transducer may be accompanied with heat generation. In particular, when the transducer includes a plurality of elements, the heat generation rate is likely to increase exponentially, and therefore the ultrasonic probe may include a heat radiation means for efficiently emitting heat.

SUMMARY

Exemplary embodiments address at least the above problems and/or disadvantages and other disadvantages not described above. Also, the exemplary embodiments are not required to overcome the disadvantages described above, and may not overcome any of the problems described above.

One or more exemplary embodiments provide an ultrasonic probe including a pulsating heat pipe in order to efficiently emit heat, and a method of manufacturing the same.

In accordance with an aspect of an exemplary embodiment, an ultrasonic probe includes: a transducer array that generates ultrasonic waves; a backing layer that is provided on a rear surface of the transducer array; a pulsating heat pipe that absorbs heat generated in the transducer array; and a heat radiation unit that receives the heat from the pulsating heat pipe to emit the received heat to the outside.

The pulsating heat pipe may include a heating unit that is inserted into the backing layer so that a working fluid is heated by the heat generated in the transducer array, a heat insulating unit through which the heated working fluid is transported, and a cooling unit that contacts the heat radiation unit so that the working fluid transported through the heat insulating unit is cooled.

The heating unit may extend from one surface of the backing layer to the other surface thereof to penetrate the backing layer.

The pulsating heat pipe may penetrate the backing layer to be exposed through the other surface of the backing layer, and the exposed portion of the pulsating heat pipe may be connected to the one surface of the backing layer.

The heating unit may be inserted to one surface of the backing layer to be exposed through the one surface of the backing layer.

Also, a portion of the pulsating heat pipe which is exposed through the one surface of the backing layer may be connected to the one surface of the backing layer via the heat radiation unit.

The transducer array may include a transducer element that is vibrated to generate ultrasonic waves, and an application specific integrated circuit (ASIC) that controls a current supplied to the transducer element.

The pulsating heat pipe may transfer heat generated in the ASIC to the heat radiation unit.

The backing layer may be constituted of a plurality of layers containing mutually different sound absorbing materials.

The pulsating heat pipe may be inserted into any one of the plurality of layers of the backing layer or any one of respective boundaries between each of the plurality of layers.

The heat radiation unit may be made of a metal material so as to absorb heat from the pulsating heat pipe.

In accordance with another aspect of an exemplary embodiment, a method of manufacturing an ultrasonic probe includes: providing a transducer array that generates ultrasonic waves; providing a backing layer on a rear surface of the transducer array; providing a pulsating heat pipe that absorbs heat generates in the transducer array; and providing a heat radiation unit that receives the heat from the pulsating heat pipe to emit the received heat to the outside.

The providing of the pulsating heat pipe may include inserting a heating unit into the backing layer so that a working fluid is heated by the heat generated in the transducer array, providing a heat insulating unit through which the heated working fluid is transported, and bring a cooling unit into contact with the heat radiation unit so that the working fluid transported through the heat insulating unit is cooled.

The inserting of the heating unit into the backing layer may include extending the heating unit from one surface of the backing layer to the other surface thereof so that the heating unit penetrates the backing layer.

The providing of the pulsating heat pipe may further include extending the cooling unit which contacts the heat radiation unit so that the cooling unit is connected to the one surface of the backing layer.

The inserting of the heating unit into the backing layer may include inserting the heating unit to one surface of the backing material so that the heating unit is exposed through the one surface of the backing material.

The providing of the pulsating heat pipe may further include extending the cooling unit which contacts the heat radiation unit so that the cooling unit is connected to the one surface of the backing layer.

The providing of the transducer array may include providing a transducer element that is vibrated to generate ultrasonic waves, and providing an ASIC that controls a current supplied to the transducer element.

The providing of the backing layer may include providing a plurality of layers containing mutually different sound absorbing materials.

The providing of the pulsating heat pipe may include inserting the pulsating heat pipe into any one of the plurality of layers of the backing layer or any one of respective boundaries between each of the plurality of layers.

The providing of the heat radiation unit may include providing the heat radiation unit made of a metal material so that the heat radiation unit absorbs heat from the pulsating heat pipe.

BRIEF DESCRIPTION OF THE DRAWINGS

The above and/or other aspects will become more apparent by describing certain exemplary embodiments with reference to the accompanying drawings, in which.

DETAILED DESCRIPTION

Figure 1:
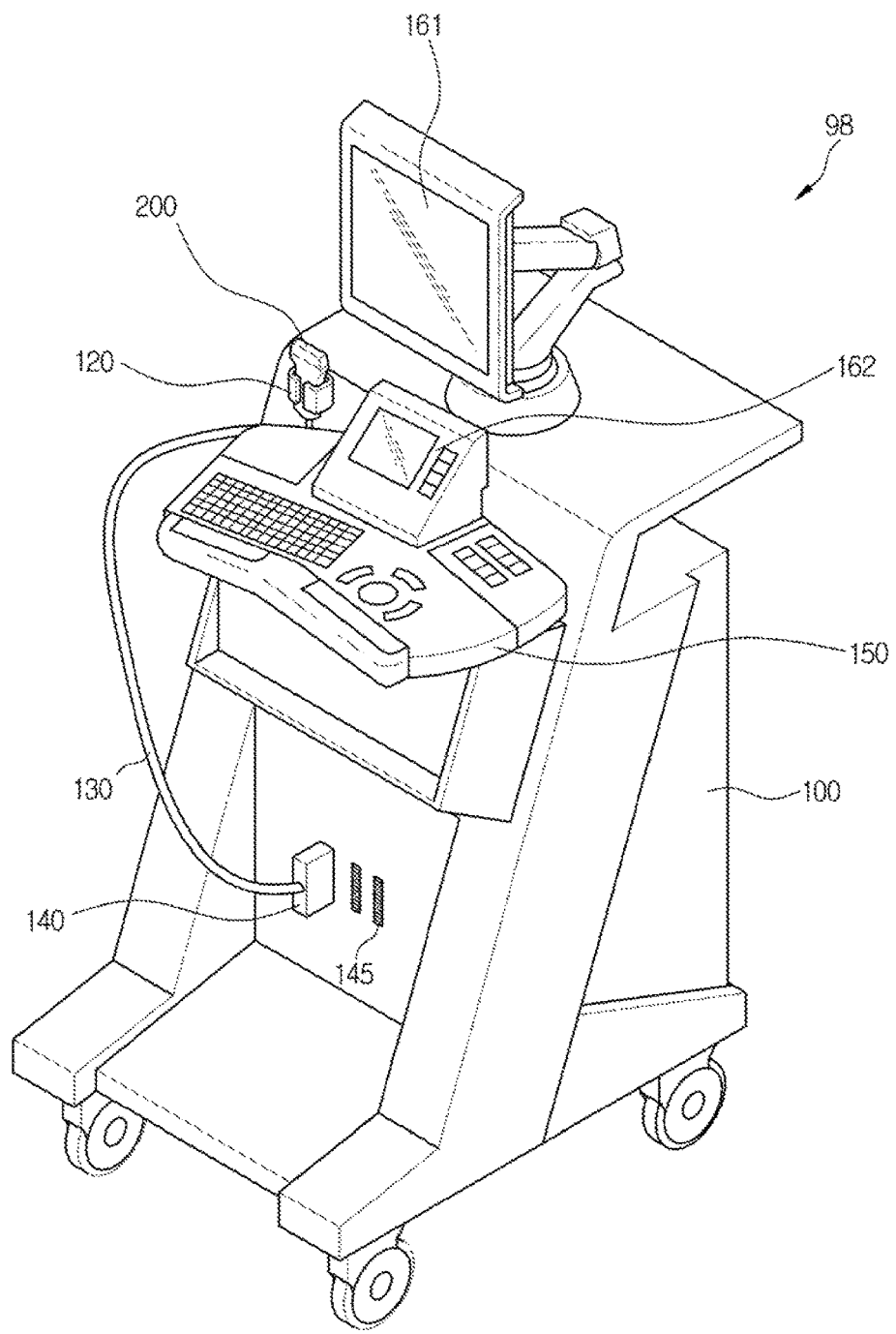
FIG. 1 is a perspective view showing an example of an ultrasonic imaging apparatus.

Certain exemplary embodiments are described in greater detail below with reference to the accompanying drawings.

In the following description, like drawing reference numerals are used for like elements, even in different drawings. The matters defined in the description, such as detailed construction and elements, are provided to assist in a comprehensive understanding of the exemplary embodiments. However, it is apparent that the exemplary embodiments can be practiced without those specifically defined matters. Also, well-known functions or constructions are not described in detail since they would obscure the description with unnecessary detail.

FIG. 1 is a perspective view showing an example of an ultrasonic imaging apparatus. As shown in FIG. 1, the ultrasonic imaging apparatus may include a main body 100, an ultrasonic probe 200, an input unit 150, and a display 160.

At least one female connector 145 may be provided on one side of the main body 100. A male connector 140 that may be connected to a cable 130 may be physically coupled to the female connector 145.

A plurality of casters (not shown) for mobility of the ultrasonic imaging apparatus may be provided on a lower side of the main body 100. The plurality of casters may fix the ultrasonic imaging apparatus in a specific place, or move the ultrasonic imaging apparatus in a specific direction. Such an ultrasonic imaging apparatus may be referred to as an ultrasonic imaging cart apparatus.

Alternatively, the ultrasonic imaging apparatus may be a portable ultrasonic imaging apparatus that may be carried when moving over a large distance. In this instance, the portable ultrasonic imaging apparatus may not include a caster. As an example of the portable ultrasonic imaging apparatus, a picture archiving and communication system (PACS) viewer, a smart phone, a laptop computer, a personal digital assistant (PDA), a tablet personal computer (PC), or the like may be provided, but an exemplary embodiment is not limited thereto.

The ultrasonic probe 200 contacts a surface of an object, and may transmit and receive ultrasonic waves. Specifically, the ultrasonic probe 200 transmits the ultrasonic waves to the inside of the object, receives echo ultrasonic waves reflected from a specific portion inside the object, and transmits the received echo ultrasonic waves to the main body 100.

One end of the cable 130 may be connected to the ultrasonic probe 200, and the male connector 140 may be connected to the other end of the cable 130. The male connector 140 that is connected to the other end of the cable 130 may be physically coupled to the female connector 145 of the main body 100.

Alternatively, the ultrasonic probe may be wirelessly connected to the main body. In this case, the ultrasonic probe may wirelessly transmit the echo ultrasonic waves received from the object. In addition, a plurality of ultrasonic probes may be connected to one main body.

An image processor that converts the echo ultrasonic waves received by the ultrasonic probe into ultrasonic images may be provided inside the main body. The image processor may be implemented as hardware such as a microprocessor, and/or software that may be embedded in the hardware.

The image processor may generate ultrasonic images through a scan conversion process for echo ultrasonic waves. The ultrasonic images may include Doppler images which represent a moving subject using the Doppler effect, images of gray scale acquired by scanning the object in an amplitude mode (A-mode), a brightness mode (B-mode), and/or a motion mode (M-mode). The Doppler images may include blood flow Doppler images (referred to as color Doppler images) representing the flow of blood, tissue Doppler images representing movement of tissues, and spectral Doppler images representing a moving speed of the object by a waveform.

The image processor may extract a B-mode component from the echo ultrasonic waves received by the ultrasonic probe, in order to generate B-mode images. The image processor may generate the ultrasonic images in which the intensity of echo ultrasonic waves is represented to be bent based on the B-mode component.

Similarly, the image processor may extract a Doppler component from the echo ultrasonic waves, and generate a Doppler image obtained by showing the movement of the object by colors or waveforms based on the extracted Doppler component.

The image processor may generate three-dimensional (3D) ultrasonic images by performing volume-rendering on volume data acquired through the echo ultrasonic waves, and generate elastic images obtained by visualizing the degree of deformation of the object in accordance with pressure. The image processor may represent a variety of additional information on the ultrasonic images by text or graphics.

The generated ultrasonic images may be stored in a memory located inside of the main body, in an external memory. Additionally or alternatively, the ultrasonic images may be stored in a web storage that performs a storage function on webs or a cloud server.

The input unit 150 may receive commands related to operations of the ultrasonic imaging apparatus. For example, the input unit 150 may receive a mode selection command such as A-mode, B-mode, M-mode, or Doppler mode (D-mode). Further, the input unit 150 may receive a command to start an ultrasonic imaging.

The command input through the input unit 150 may be transmitted to the main body through wired or wireless communication.

The input unit 150 may include at least one of a keyboard, a foot switch, and a foot pedal. The keyboard may be implemented as hardware to be positioned on an upper portion of the main body 100. Such a keyboard may include at least one of a switch, keys, joystick, and a trackball. As another example, the keyboard may be implemented as software such as a graphic user interface (GUI). In this case, the keyboard may be displayed through a sub display 162 or a main display 161. The foot switch or the foot pedal may be provided in a lower portion of the main body 100, and a user may control operations of the ultrasonic imaging apparatus using the foot pedal.

The display 160 may include the main display 161 and the sub display 162.

The sub display 162 may be provided in the main body 100. In FIG. 1, a case in which the sub display 162 is provided in the upper portion of the main body 100 is shown. The sub display 162 may display applications related to operations of the ultrasonic imaging apparatus. For example, the sub display 162 may display a menu, instructions, and the like required for an ultrasonic diagnosis. Such a sub display 162 may include a cathode ray tube (CRT), a liquid crystal display (LCD), or the like.

The main display 161 may be provided on the main body 100. In FIG. 1, a case in which the main display 161 is provided above the sub display 162 is shown. The main display 161 may display ultrasonic images obtained in an ultrasonic diagnostic process, in accordance with an input applied to the input unit. Such a main display 161 may be implemented by a CRT or LCD in the same manner as in the sub display 162. In FIG. 1, a case in which the main display 161 is coupled to the main body 100 is shown, but the main display 161 may be implemented to be detachable from the main body 100.

In FIG. 1, a case in which the main display 161 and the sub display 162 are all provided in the ultrasonic imaging apparatus is shown, but the sub display 162 may be omitted. In this case, the application or menu displayed through the sub display 162 may be displayed through the main display 161.

The ultrasonic imaging apparatus may further include a communication unit. The communication unit is connected to a network in a wired or wireless manner to communicate with an external device or server. The communication unit may transmit and receive data to and from a hospital's server or other medical apparatuses in the hospital which is connected through a picture archiving and communication system (PACS). The communication unit may perform data communication in accordance with the digital imaging and communications in medicine (DICOM) standard.

The communication unit may transmit and receive data related to a diagnosis of the object such as ultrasonic images of the object, echo ultrasonic waves, Doppler data, and the like through the network, and also transmit and receive medical images obtained by other medical apparatuses such as a CT, an MRI, an X-ray, and the like. Further, the communication unit may receive information related to a patient's diagnostic history or treatment schedule from the server to utilize the received information in the diagnosis of the object. Furthermore, the communication unit may perform data communication with portable terminals of physicians or patients as well as the hospital's server or other medical apparatuses.

The communication unit may be connected to the network in the wired or wireless manner to transmit and receive data to and from the server, the medical apparatuses, and/or the portable terminal. The communication unit may include at least one component capable of performing communication with an external device, and include, for example, a short-range communication module, a wired communication module, and a mobile communication module.

The short-range communication module refers to a module for short-range communication within a predetermined distance. As examples of short-range communication technology in accordance with an exemplary embodiment, wireless LAN, Wi-Fi, Bluetooth, ZigBee, Wi-Fi direct (WFD), ultra wideband (UWB), infrared data association (IrDA), Bluetooth low energy (BLE), near field communication (NFC), and the like may be provided, but an exemplary embodiment is not limited thereto.

The wired communication module refers to communication using electric signals or optical signals, and as examples of wired communication technology, a pair cable, a coaxial cable, an optical fiber cable, an Ethernet cable, and the like may be provided.

The mobile communication module transmits and receives radio signals with at least one of a base station, an external terminal, and a server on a mobile communication network. The radio signals may include voice call signals, video call signals, or various types of data depending on transmission and reception of text/multimedia messages.

Hereinafter, an example of an ultrasonic probe in accordance with an arrangement of transducer elements will be described with reference to FIGS. 2A and 2B.

Figure 2A:
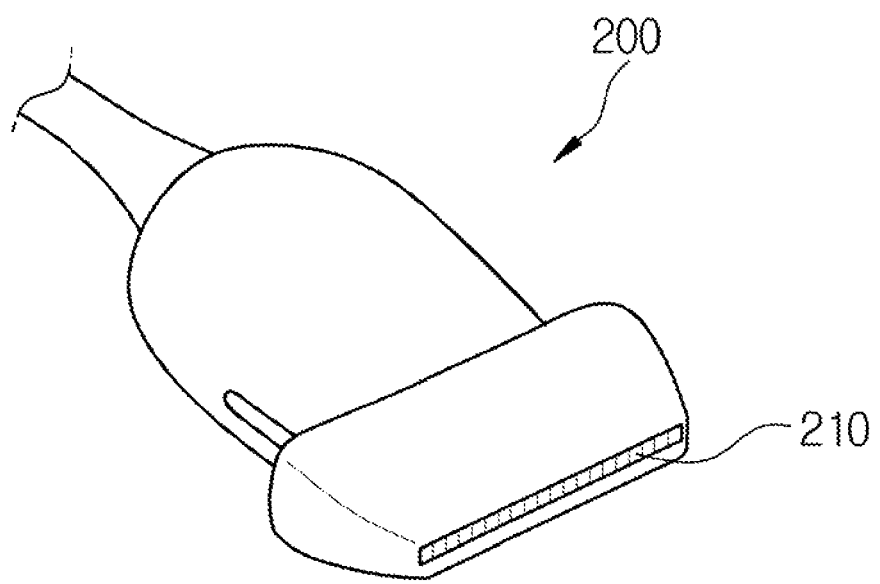
FIG. 2A is a view showing the appearance of a 1D array probe in accordance with an exemplary embodiment.
Figure 2B:
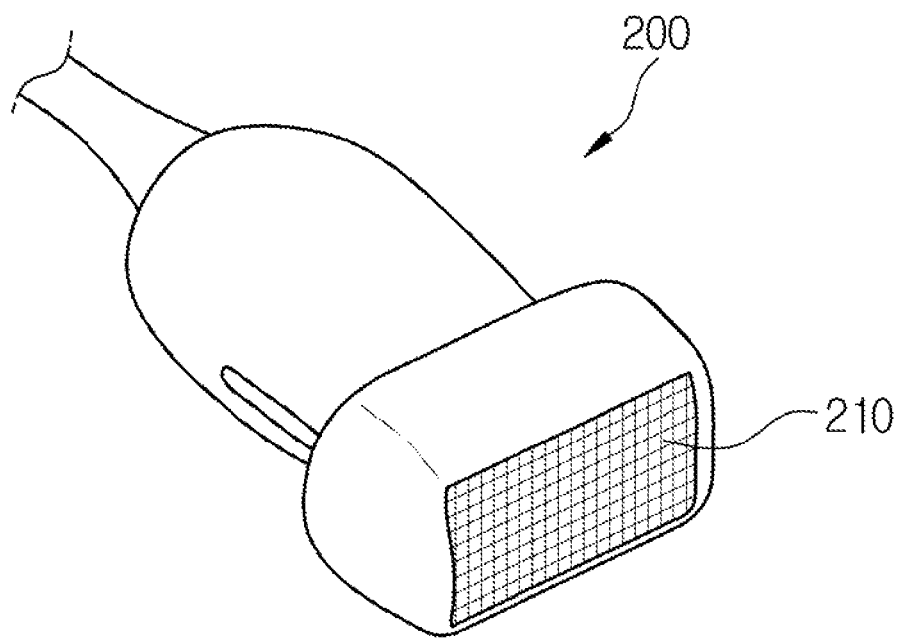
FIG. 2B is a view showing the appearance of a 2D array probe in accordance with an exemplary embodiment.

FIG. 2A is a view showing the appearance of a 1D array probe in accordance with an exemplary embodiment, and FIG. 2B is a view showing the appearance of a 2D array probe in accordance with an exemplary embodiment.

The type of an ultrasonic probe 200 may be classified in accordance with an arrangement of transducer elements 210. Referring to FIG. 2A, a case in which the transducer elements 211 are arranged in one-dimensional manner on one surface of the ultrasonic probe 200 is referred to as a 1D array probe. The 1D array probe includes a linear array probe in which the transducer elements 210 are arranged in a straight line, a phased array probe, and a convex array probe in which the transducer elements 210 are arranged in a curved line.

A case in which the transducer elements 211 are arranged in a two-dimensional manner is referred to as a 2D array probe. As shown in FIG. 2B, in the 2D array probe, the transducer elements 211 may be arranged on a plane. Alternatively, the transducer elements 211 may be arranged while forming a curved surface on one surface of the 2D array probe.

The transducer arranged in the ultrasonic probe 200 may be vibrated while transmitting and receiving ultrasonic waves, and in this instance, heat generation may be accompanied by the vibration. In particular, in a case of the 2D array probe, since the number of the transducer elements 211 is greater than that in the 1D array probe, the heat generation rate may be increased.

The heat may be transmitted to a lens provided in front of the ultrasonic probe 200. The lens is a portion which is brought into directly contact with the patient's skin, and therefore when heat inside the ultrasonic probe 200 is directly transmitted to the patient, the skin tissue of the patient which contacts the ultrasonic probe 200 may be damaged.

In addition, when a high-temperature state is maintained inside the ultrasonic probe 200, it may cause performance degradation of components provided in the ultrasonic probe 200. This may be an obstacle to obtaining accurate ultrasonic images, and an ultrasonic diagnosis based on the ultrasonic images may cause inaccurate results which ultimately create a negative influence on the safety of the patient. Thus, in the ultrasonic probe 200, a means for efficiently radiating the heat should be provided.

Hereinafter, an example of the ultrasonic probe 200 including a heat radiation means will be described.

Figure 3A:
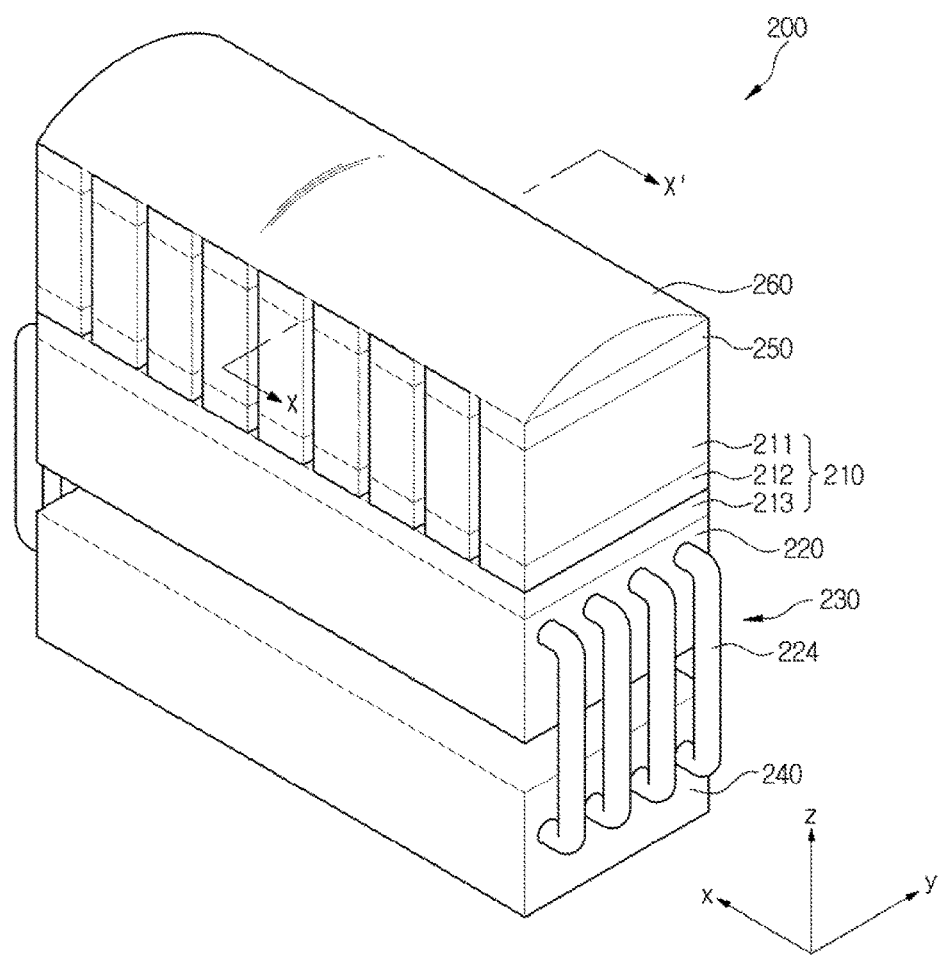
FIGS. 3A and 3B are schematic perspective views a configuration of an ultrasonic probe in accordance with an exemplary embodiment.
Figure 3B:
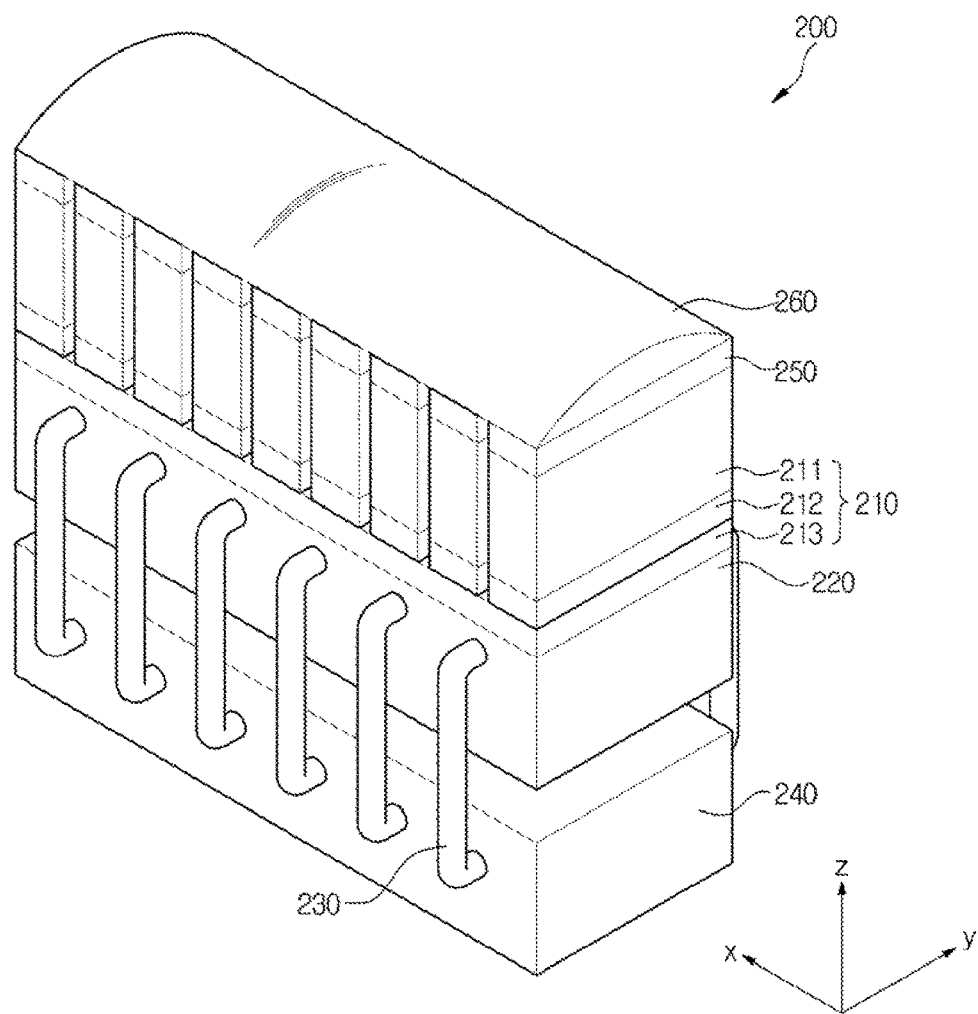

FIGS. 3A and 3B are schematic perspective views showing configurations of the ultrasonic probe 200 in accordance with an exemplary embodiment.

The ultrasonic probe 200 in accordance with an exemplary embodiment may include a transducer array 210 that generates ultrasonic waves, a backing layer 220 that is provided on a rear surface of the transducer array, a pulsating heat pipe 230 that absorbs heat generated in the transducer array, and a heat radiation unit 240 that receives heat from the pulsating heat pipe to emit the received heat to the outside.

The ultrasonic probe 200 may further include a matching layer 250 that reduces a difference of acoustic impedance between the transducer array 210 and an object so that the ultrasonic waves generated in the transducer array 210 are efficiently transmitted onto the object, and a lens 260 that focuses ultrasonic waves generated in the transducer.

The transducer array 210 may generate ultrasonic waves to transmit the generated ultrasonic waves onto the object or receive echo ultrasonic waves reflected from the object. For this, the transducer array 210 may include a transducer element 211 that is vibrated to generate ultrasonic waves, and an application specific integrated circuit (ASIC) 212 that controls a current supplied to the transducer element.

The transducer element 211 may include a piezoelectric ultrasonic transducer using the piezoelectric effect of a piezoelectric material, a magnetostrictive ultrasonic transducer using the magnetostrictive effect of a magnetic material, and a capacitive micromachined ultrasonic transducer (hereinafter referred to as a "cMUT") that receives acoustic waves using vibrations of several hundreds or thousands of micromachined thin films.

The transducer element 211 may directly receive the supply of the current. Alternatively, the transducer element 211 may receive the supply of the current through the ASIC 212. For example, the current supplied to each of the transducer elements through the ASIC 212 is controlled. When applying integration technology through the ASIC 212, the reliability of the ultrasonic probe 200 and ultrasonic imaging apparatus may be increased and the complexity of the ultrasonic probe 200 may be reduced, thereby obtaining excellent signal processing efficiency.

The ASIC 212 may be provided on a printed circuit board 213 to receive the supply of the current from a power source.

The backing layer 220 may be provided on a rear surface of the transducer array 210 so as to block ultrasonic waves advancing toward the rear surface of the transducer array 210 rather than the front surface thereof. Through this, a distortion of the ultrasonic images may be prevented in advance.

In FIGS. 3A and 3B, a case in which the backing layer 220 is provided so as to contact the printed circuit board in which the ASIC 212 of the transducer array 210 is provided is shown. However, the ASIC 212 and the printed circuit board may be formed on a side surface of the transducer array 210, and the backing layer 220 may be brought into direct contact with the transducer element 211.

The pulsating heat pipe 230 may absorb heat generated in the transducer array 210. The pulsating heat pipe 230 may absorb the heat generated in the ASIC 212 and in the transducer element 211 and control a temperature inside the ultrasonic probe 200.

The pulsating heat pipe 230 does not need a wick structure for transporting a working fluid therein unlike a general heat pipe, and therefore the manufacturing costs are reduced due to a simple manufacturing process, and the pulsating heat pipe 230 may use an ultra-small diameter tube to withstand high pressure and have elasticity to have a small limitation in its installation space.

The pulsating heat pipe 230 may use a small diameter tube having an inner diameter of approximately 1 mm, and charge the working fluid to the small diameter tube which is in a vacuum state, at an arbitrary ratio. When the working fluid is heated inside the small diameter tube to cause an occurrence of nucleate boiling, vapor bubbles generated by the nucleate boiling are added to the working fluid to obtain gas-liquid slugs. The slugs are axially oscillated while generating pressure waves, and circulated inside the small diameter tube. In this instance, the vapor bubbles may transport heat by performing convective heat transfer and latent heat transportation. That is, the pulsating heat pipe 230 may rapidly transfer heat by a two-phase flow by the evaporation and condensation of the working fluid.

The pulsating heat pipe may be provided in the form of a small diameter pipe containing a metal having excellent thermal conductivity. For example, the pulsating heat pipe may be provided in the form of a copper (Cu) small diameter pipe. The copper has excellent thermal conductivity, and thereby may absorb external heat well and emit heat to the outside well.

Alternatively, the pulsating heat pipe may contain an alloy of copper and aluminum (Al). In this case, as the working fluid, acetone having low reactivity with aluminum may be used.

However, the pulsating heat pipe is not necessarily made of a metal. For example, the pulsating heat pipe may contain a metal and a non-metal or only the non-metal.

The pulsating heat pipe 230 may be provided to be an open loop type or a closed loop type. Hereinafter, for convenience, descriptions will be made assuming the closed loop type pulsating heat pipe 230.

The pulsating heat pipe 230 may include a heating unit 222 that is inserted into the backing layer 220 so that the working fluid is heated by the heat generated in the transducer array 210, a heat insulating unit 224 through which the heated working fluid is transported, and a cooling unit 226 that contacts the heat radiation unit so that the working fluid transported through the heat insulating unit is cooled.

Referring to FIG. 3A, the heating unit may be inserted through the surface that extends in a Y-axis direction different from an X-axis direction in which the transducer elements 211 are arranged, among side surfaces of the backing layer 220. Alternatively, as shown in FIG. 3B, the heating unit may be inserted through the surface that extends in the X-axis direction in which the transducer elements 211 are arranged, among the side surfaces of the backing layer 220.

In addition, in FIGS. 3A and 3B, a case in which the heating unit is inserted through two surfaces of the backing layer is shown, but unlike this, the heating unit may be inserted through a single surface or at least three surfaces of the backing layer 220.

The heating unit may be inserted into the backing layer 220, and therefore, when the heat generated in the transducer array 210 is transmitted to the backing layer 220, the transmitted heat may be absorbed in the heating unit. Specifically, the heat generated in the transducer array 210 may be transmitted to the backing layer 220, and the working fluid of the heating unit may be heated by the transmitted heat.

The heating unit may be implemented in various manners within the technical concept in which the heating unit is inserted into the backing layer 220 so as to absorb the heat generated in the transducer array 210.

Hereinafter, a method in which the heating unit is inserted into the backing layer 220 will be described with reference to FIGS. 4 and 5.

Figure 4:
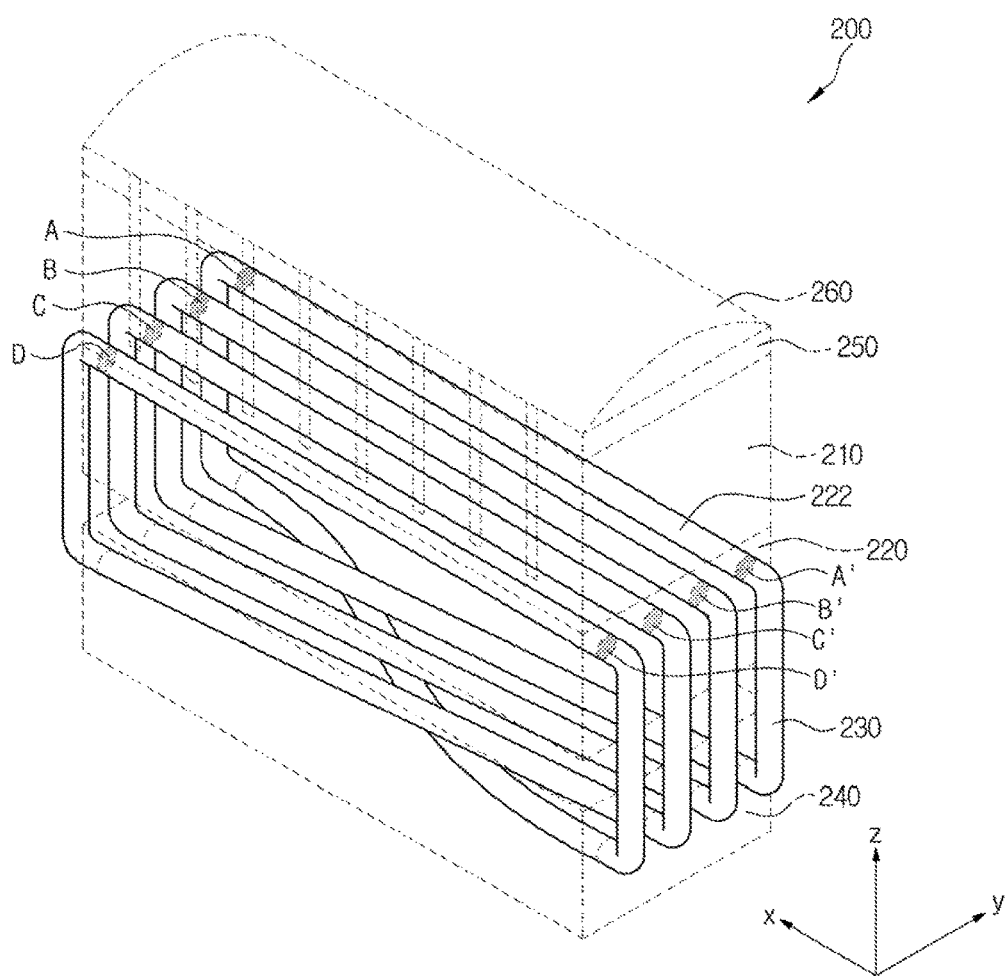
FIG. 4 is a view showing a structure of a pulsating heat pipe in an ultrasonic probe including one pulsating heat pipe in accordance with an exemplary embodiment.

FIG. 4 is a view showing a structure of a pulsating heat pipe in an ultrasonic probe 200 including one pulsating heat pipe in accordance with an exemplary embodiment.

The heating unit 222 may extend from one surface of the backing layer 220 to the other surface thereof to penetrate the backing layer 220. In FIG. 4, a case in which the pulsating heat pipe 230 penetrates the backing layer 220 four times (through A and A', B and B', C and C', and D and D') is shown.

The pulsating heat pipe 230 penetrating through the backing layer 220 may be exposed through the other surface of the backing layer 220, and the exposed pulsating heat pipe 230 may be provided so as to penetrate the backing layer 220 through the one surface of the backing layer 220 again.

For example, referring to FIG. 4, the pulsating heat pipe 230 that penetrates from A of the one surface of the backing layer 220 to A' of the other surface thereof may be connected from A' to B of one surface of the backing layer 220, and thereby may penetrate the backing layer 220 again and be exposed through B' of the other surface. The pulsating heat pipe exposed through B' may penetrate the backing layer 220 through C of one surface of the backing layer 220 and be exposed to the outside through C'. In the same manner, the exposed pulsating heat pipe 230 may be connected to D of one surface of the backing layer 220 and penetrate the backing layer from D to D' of the other surface. Finally, the pulsating heat pipe 230 exposed through D' may be connected to A of one surface of the backing layer 220 to form a single closed loop.

Unlike this, a plurality of separate pulsating heat pipes 230 may be provided in the ultrasonic probe 200.

Figure 5:
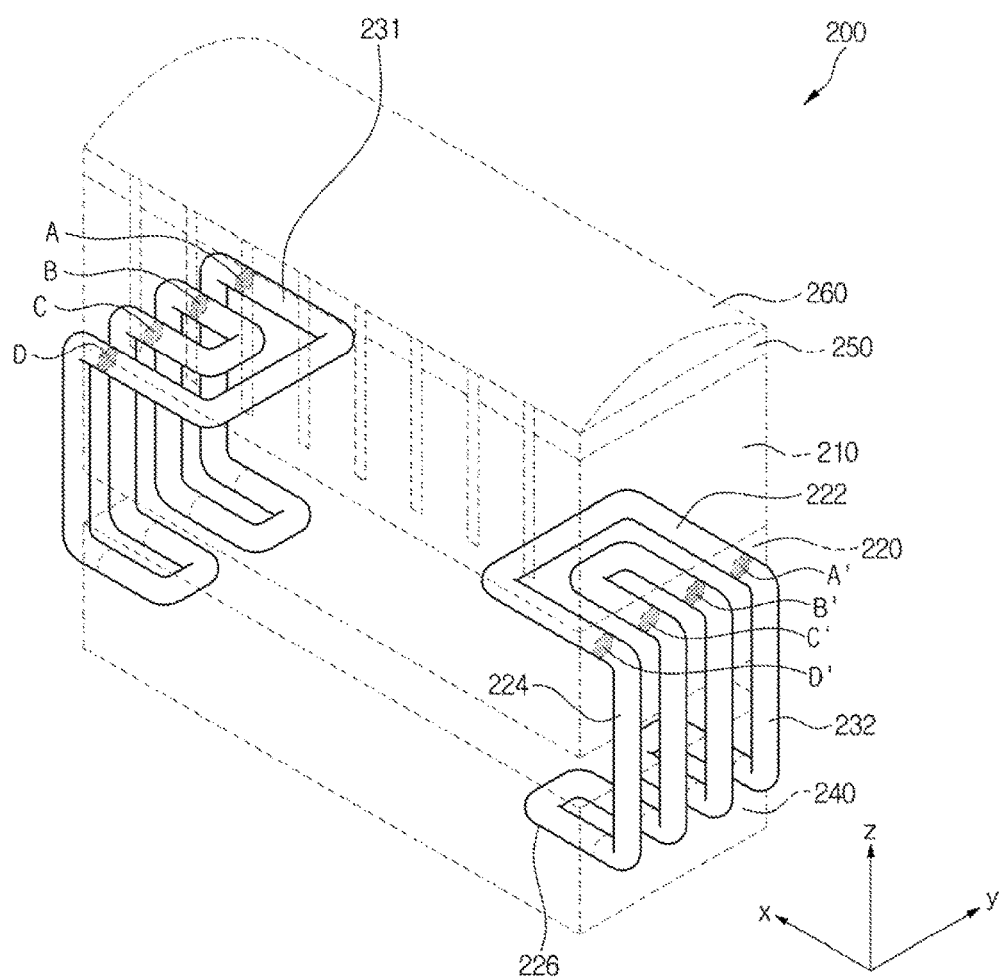
FIG. 5 is a view showing a structure of a pulsating heat pipe in an ultrasonic probe including two pulsating heat pipes in accordance with an exemplary embodiment.

FIG. 5 is a view showing a structure of a pulsating heat pipe in the ultrasonic probe 200 including two pulsating heat pipes in accordance with an exemplary embodiment. The ultrasonic probe 200 of FIG. 5 includes a first pulsating heat pipe 231 and a second pulsating heat pipe 232.

Each of the two pulsating heat pipes 231 and 232 may be inserted into the backing layer 220 through different surfaces, for example, surfaces opposing one another. That is, the heating unit included in the first pulsating heat pipe 231 may be inserted into the backing layer 220 through one surface of the backing layer 220 and exposed through the one surface. The heating unit included in the second pulsating heat pipe 232 may be inserted into the backing layer 220 through the other surface thereof and exposed through the other surface.

Unlike this, the heating unit included in the second pulsating heat pipe 232 may be inserted into the backing layer 220 through the one surface of the backing layer 220 and exposed through the one surface in the same manner as in the first pulsating heat pipe 231.

Referring to FIG. 5, the first pulsating heat pipe 231 may be inserted into the backing layer 220 through one surface of the backing layer 220 and exposed through D of the one surface of the backing layer 220 via the inside of the backing layer 220. The first pulsating heat pipe 231 exposed in this manner may be connected to C of the one surface of the backing layer 220 outside the backing layer 220. Further, the first pulsating heat pipe 231 may be inserted into the backing layer 220 through C of the one surface of the backing layer 220 and exposed through B of one surface of the backing layer 220. Finally, the first pulsating heat pipe 231 exposed through B of the one surface of the backing layer 220 may be connected to A of one surface of the backing layer 220 outside the backing layer 220 to thereby form a single closed loop.

In the same manner as in the first pulsating heat pipe 231, the second pulsating heat pipe 232 may also be provided. As a result, the second pulsating heat pipe 232 may also form a single closed loop.

The method in which the heating unit is inserted into the backing layer 220 has been described with reference to FIGS. 4 and 5, but is merely an example, and thus an exemplary embodiment is not limited thereto. Thus, any method in which the heating unit 222 is inserted into the backing layer so that the working fluid is heated by the heat generated in the transducer array 210 may be possible.

Referring again to FIGS. 3A and 3B, one end of the heat insulating unit 224 may extend from the heating unit outside the backing layer 220. The working fluid of the heating unit heated inside the backing layer 220 may be transported to the outside of the backing layer 220. This means that the heat generated in the transducer array 210 is transported to the outside of the backing layer 220 along the heat insulating unit.

The other end of the heat insulating unit may be connected to the cooling unit. Thus, the heated working fluid may be transmitted to the cooling unit through the heat insulating unit.

The cooling unit may be formed so as to contact the heat radiation unit 240 so that the working fluid transported through the heat insulating unit can be cooled. When the working fluid reaches the cooling unit, the working fluid may be cooled by the heat radiation unit 240. This means that the heat generated in the transducer array 210 is emitted by the heat radiation unit 240.

The cooling unit may contact the heat radiation unit 240 in various methods. In FIG. 3A, a case in which the cooling unit is inserted into the heat radiation unit 240 is shown. Thus, the cooling unit may be inserted into the heat radiation unit 240 through one surface of the heat radiation unit 240 to contact the heat radiation unit 240.

Alternatively, the cooling unit may contact the surface of the heat radiation unit 240 in another contact method.

Figure 6:
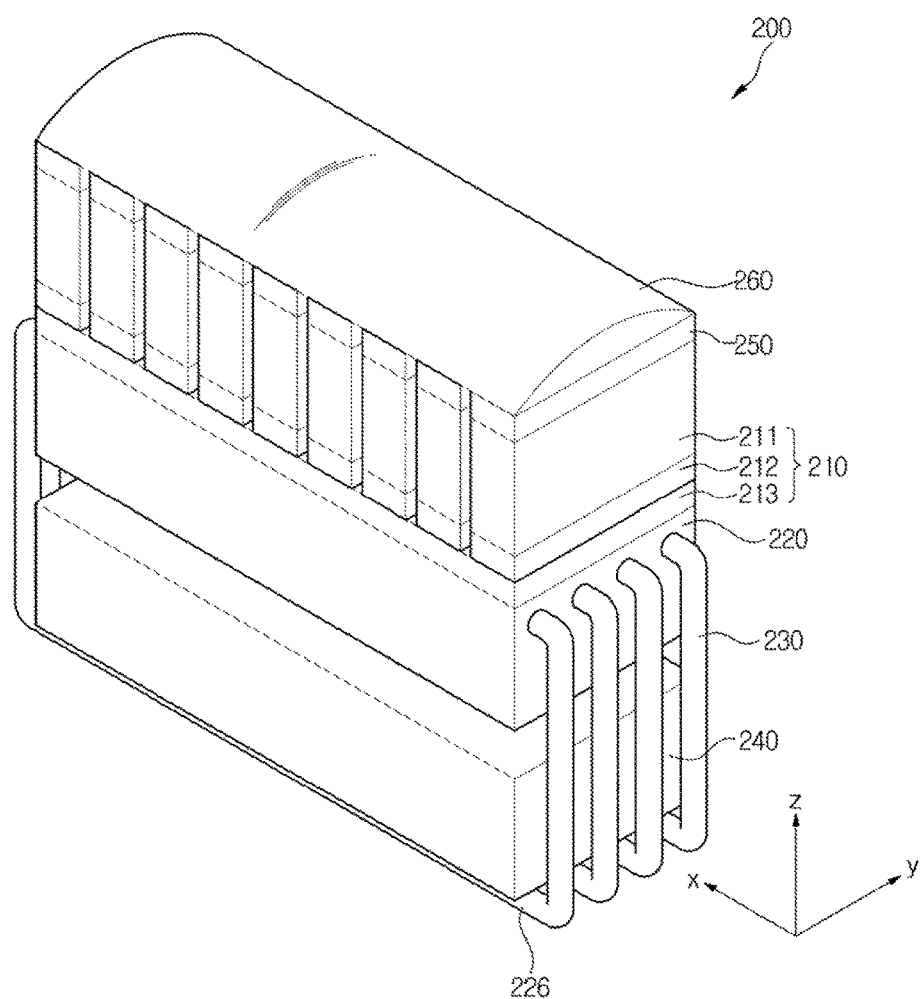
FIG. 6 is a view showing a contact method of a cooling unit with a heat radiation unit of an ultrasonic probe in accordance with an exemplary embodiment.

FIG. 6 is a view showing a contact method of the cooling unit with the heat radiation unit 240 of the ultrasonic probe 200 in accordance with an exemplary embodiment.

As shown in FIG. 6, the cooling unit 226 may be provided so as to contact the surface of the heat radiation unit 240 without being inserted into the heat radiation unit 240. The method of FIG. 6 is merely an example of the contact method of the cooling unit with the surface of the heat radiation unit 240, and thus the cooling unit may contact the surface of the heat radiation unit 240 in various methods.

The working fluid of the cooling unit that contacts the heat radiation unit 240 may be cooled by the heat radiation unit 240. That is, the heat of the working fluid transported to the cooling unit may be transmitted to the heat radiation unit 240. For this, the heat radiation unit 240 may be provided in the form of a metal block having high thermal conductivity.

The heat radiation unit 240 may be connected to a heat sink to emit heat to the outside. Alternatively, the heat radiation unit 240 may be connected to a housing of the ultrasonic probe 200 to emit heat to the outside.

As shown in FIGS. 3A and 3B, in the ultrasonic probe 200 including the pulsating heat pipe 230 for heat radiation, the design freedom of the backing layer 220 may be increased. The related art backing layer 220 performs the heat radiation function as well as the sound absorbing function, and thereby may be provided in the form of a combination of a sound absorbing material performing the sound absorbing function and a metal powder performing the heat radiation function. However, in the ultrasonic probe 200 of an exemplary embodiment which includes the pulsating heat pipe 230, the pulsating heat pipe 230 performs the heat radiation function, and therefore the backing layer 220 may be made of only the sound absorbing material, and therefore the design freedom of the backing layer 220 may be increased.

Hereinafter, in the ultrasonic probe 200 including the pulsating heat pipe 230, various examples of the backing layer 220 will be described with reference to FIGS. 7 and 8.

Figure 7A:
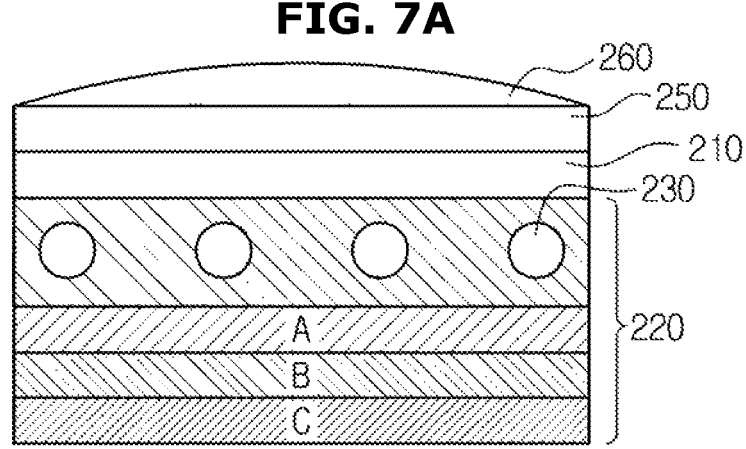
FIGS. 7A, 7B, and 7C are views showing various examples for improving heat radiation performance of a backing layer of an ultrasonic probe in accordance with an exemplary embodiment.
Figure 7B:
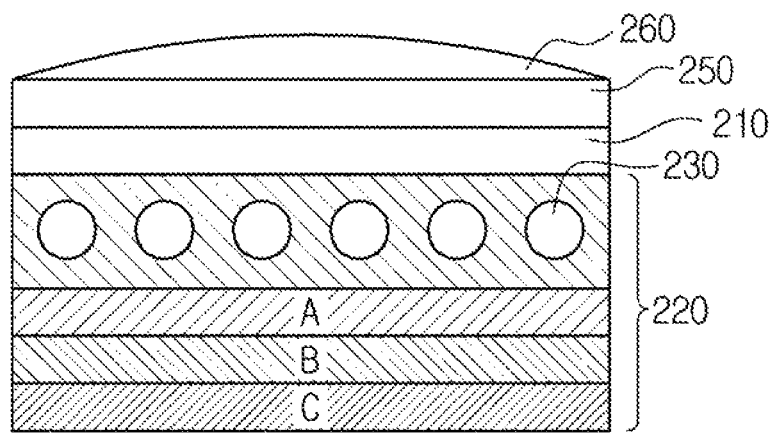
Figure 7C:
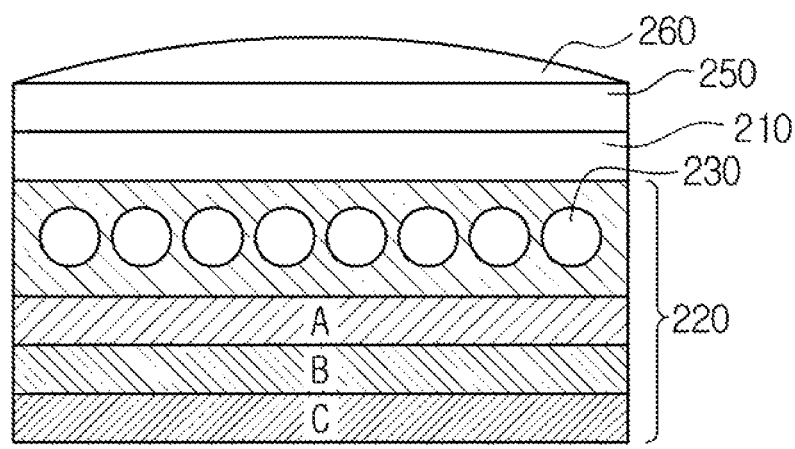

FIGS. 7A, 7B, and 7C are views showing various examples for improving heat radiation performance of the backing layer 220 of the ultrasonic probe 200 in accordance with an exemplary embodiment. FIGS. 7A, 7B, and 7C are views showing cross sectional views taken along line X-X' of FIG. 3A.

As described above, the backing layer 220 may be provided on the rear surface of the transducer array 210. When the backing layer 220 is provided in the form of a combination of the sound absorbing material and the heat radiation material, a ratio between the heat radiation material and sound absorbing material should be considered even when increasing the heat radiation performance. However, in the ultrasonic probe 200 including the pulsating heat pipe 230, by increasing the number of times in which the pulsating heat pipe 230 is inserted into the backing layer 220 made of only the sound absorbing material, the heat radiation performance may be adjusted.

For example, when the heat generation rate of the transducer array 210 is not large, the number of times in which the pulsating heat pipe 230 is inserted into the backing layer 220 may be reduced. On the other hand, when the heat generation rate of the transducer array 210 is large, by increasing the number of times in which the pulsating heat pipe 230 is inserted into the backing layer 220, a contact area with the backing layer 220 may be increased, thereby increasing the heat radiation performance.

In FIG. 7A, a case in which the pulsating heat pipe 230 is inserted into the backing layer 220 four times is shown. In order to obtain a higher heat radiation performance, as shown in FIG. 7B, the pulsating heat pipe 230 may be inserted into the backing layer 220 six times. To obtain an even higher heat radiation performance, the pulsating heat pipe 230 may be inserted into the backing layer 220 eight times, as shown in FIG. 7C.

The pulsating heat pipe 230 may be inserted so as to form a plurality of layers inside the backing layer 220.

Figure 8A:
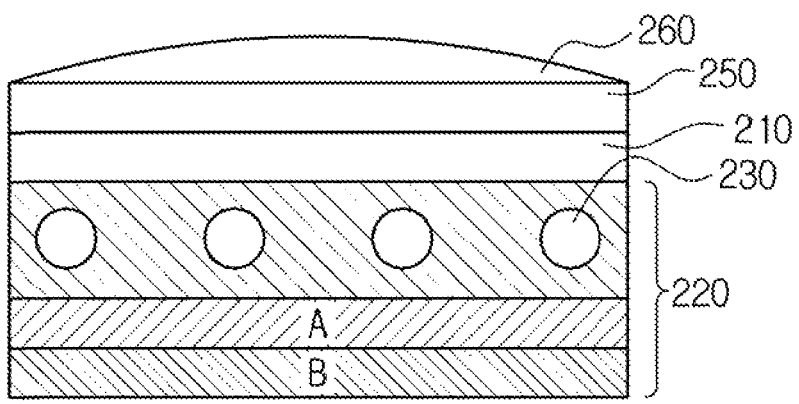
FIGS. 8A, 8B, and 8C are views showing various examples for improving sound absorbing performance of a backing layer in accordance with an exemplary embodiment.
Figure 8B:
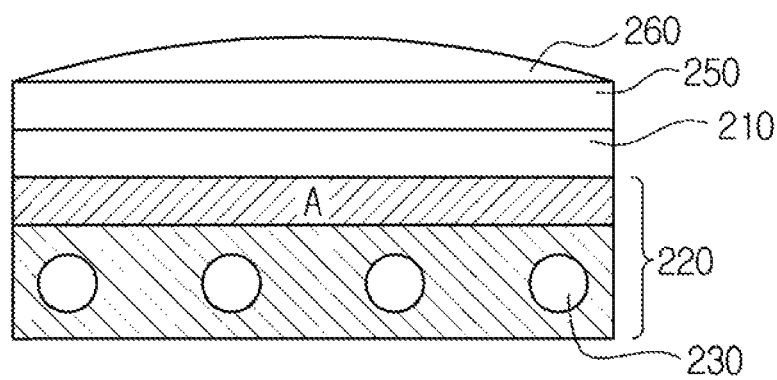
Figure 8C:
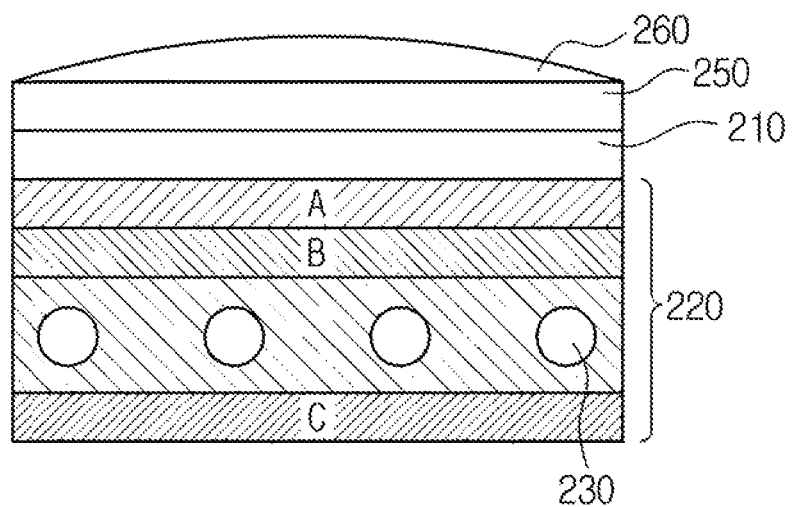

FIGS. 8A, 8B, and 8C are views showing various examples for improving sound absorbing performance of the backing layer 220 of the ultrasonic probe 200 in accordance with an exemplary embodiment. FIGS. 8A, 8B, and 8C are cross-sectional views taken along line X-X' of FIG. 3A.

When the backing layer 220 is provided in the form of a combination of the sound absorbing material and the heat radiation material, a ratio between the heat radiation material and the sound absorbing material should be considered when increasing the sound absorbing performance in the same manner as the heat radiation performance. However, in the ultrasonic probe 200 including the pulsating heat pipe 230, the sound absorbing performance may be adjusted by varying the sound absorbing material constituting the backing layer 220.

Each of the sound absorbing materials constituting the backing layer 220 may have excellent sound absorbing performance with respect to ultrasonic waves of mutually different frequency bands. Thus, the backing layer 220 may be constituted of a plurality of layers containing mutually different sound absorbing materials. By varying the arrangement of the plurality of layers, the sound absorbing performance may be adjusted.

That is, when the backing layer 220 performs only the sound absorbing function unlike a case in which the backing layer 220 simultaneously performs the sound absorbing function and the heat radiation function, the backing layer 220 may be constituted of a plurality of layers containing sound absorbing materials having excellent performance of absorbing ultrasonic waves of a desired frequency band.

For example, a material A has excellent sound absorbing performance with respect to ultrasonic waves of a first arbitrary frequency area, a material B has excellent sound absorbing performance with respect to ultrasonic waves of a second arbitrary frequency area, and a material C has excellent sound absorbing performance with respect to ultrasonic waves of a third arbitrary frequency area.

In order to obtain the excellent sound absorbing performance with respect to the ultrasonic waves of the first and second frequency areas, the backing layer 220 may be constituted of layers A and B containing the materials A and B. For example, if it is determined that the heat radiation performance is more important than the sound absorbing performance, the pulsating heat pipe 230 may be inserted into a portion of the backing layer 220 closest to the transducer array 210, as shown in FIG. 8A.

As shown in FIG. 8B, the layer A may be formed to be closer or adjacent to the transducer array 210 than the pulsating heat pipe 230. When absorbing the ultrasonic waves of the first frequency area is determined to be more important than the heat radiation function, the layer A is disposed closest to the transducer array 210, and the pulsating heat pipe 230 may be inserted into the rear surface of the layer A.

The pulsating heat pipe 230 may be inserted between the plurality of layers inside the backing layer 220. As shown in FIG. 8C, the pulsating heat pipe 230 may be inserted between the layers B and C.

As another example, the pulsating heat pipe 230 may be inserted into boundaries of the plurality of layers inside the backing layer 220. For example, the pulsating heat pipe 230 may be inserted into the boundary of the B and C layers to contact both the B and C layers.

In this manner, the internal design of the backing layer 220 may be freely selected based on the purpose of use, the performance, or the application of the ultrasonic probe 200.

As above, various examples of the backing layer 220 in the ultrasonic probe 200 including the pulsating heat pipe 230 have been described. Hereinafter, a flow of heat radiation in the ultrasonic probe 200 including the pulsating heat pipe 230 will be described.

Figure 9A:
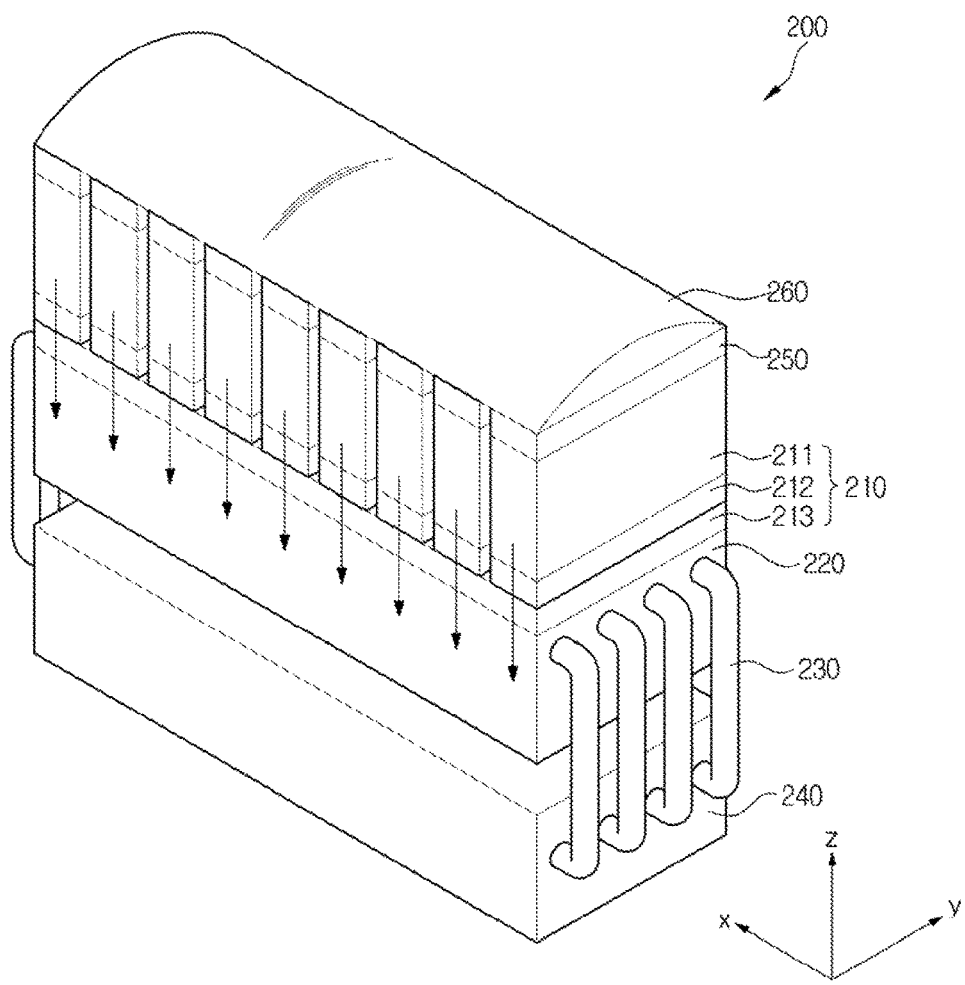
FIGS. 9A, 9B, and 9C are views showing a flow of heat radiation of an ultrasonic probe in accordance with an exemplary embodiment.
Figure 9B:
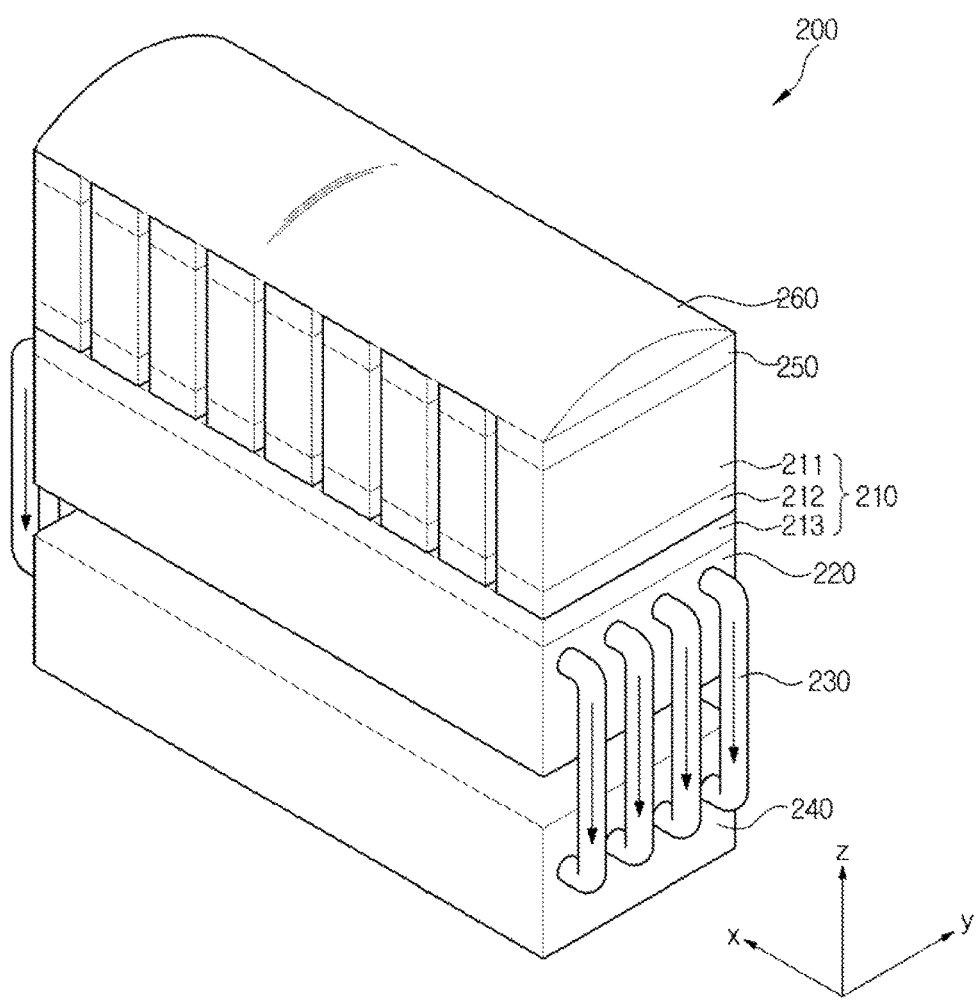
Figure 9C:
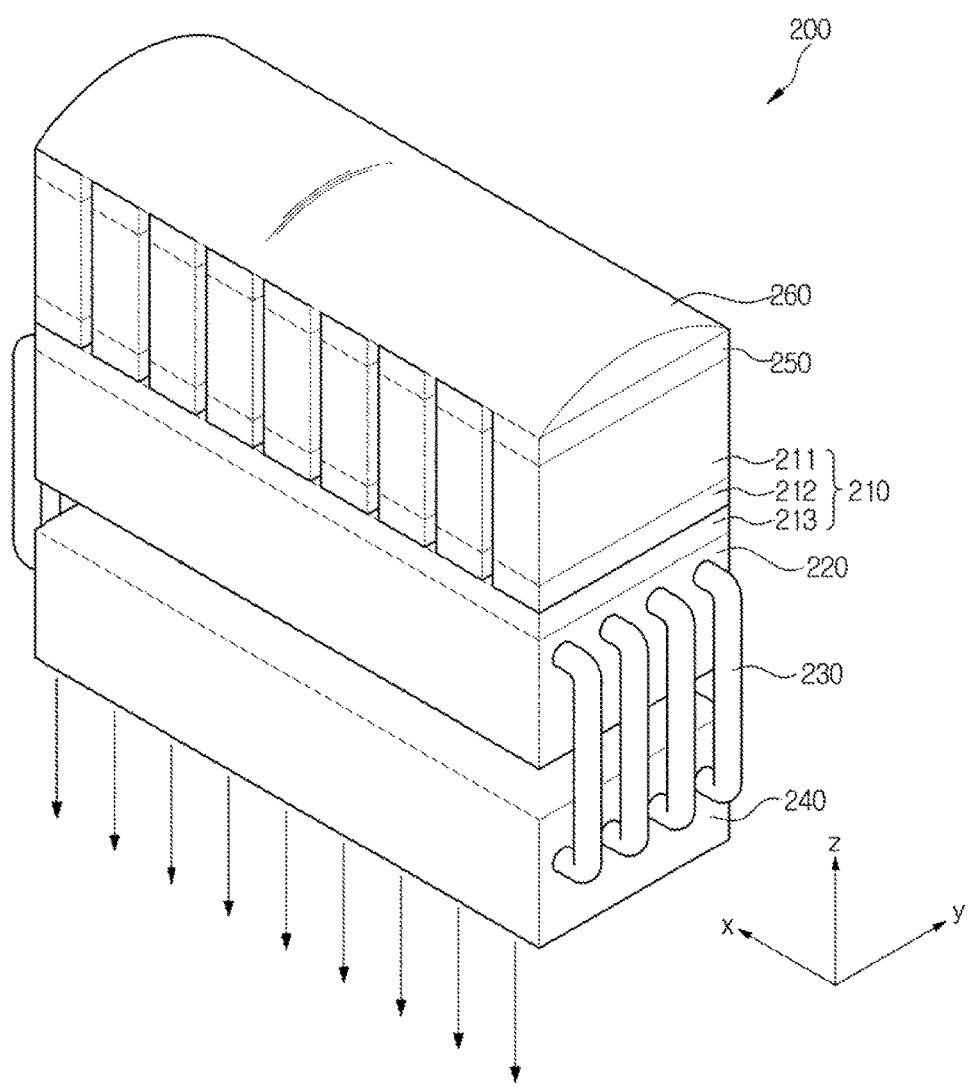

FIGS. 9A, 9B, and 9C are views showing a flow of heat radiation of the ultrasonic probe 200 in accordance with an exemplary embodiment. In FIGS. 9A, 9B, and 9C, arrows indicate advancing direction of heat.

As shown by arrows in FIG. 9A, the heat generated in the transducer array 210 may be transmitted to the backing layer 220. For a greater number of the transducer elements 211, an amount of current supplied to the transducer elements increases and, thus, the heat generation rate of the ASIC 212 that transmits a current to the transducer elements 211 may be increased. The heat may cause performance degradation of the ultrasonic probe 200 and may cause damage to the patient's skin tissue upon contact with the ultrasonic probe 200.

Referring to FIG. 9B, the heat transmitted to the backing layer 220 (as shown in FIG. 9A) may be further transmitted to the heat radiation unit 240 through the pulsating heat pipe 230. In order to absorb the heat transmitted to the backing layer 220, the pulsating heat pipe 230 may be inserted into the backing layer 220, and the pulsating heat pipe 230 may transmit the absorbed heat to the heat radiation unit 240 to emit the heat to the outside.

As shown in FIG. 9C, the heat radiation unit 240 may receive the heat absorbed by the pulsating heat pipe 230 to emit the received heat to the outside. The heat radiation unit 240 may be connected to the heat sink to emit the heat, or connected to the housing of the ultrasonic probe 200 to emit the heat to the outside, as shown by the arrows.

In this manner, the ultrasonic probe 200 including the pulsating heat pipe 230 may efficiently emit the heat generated in the transducer array 210 to the outside.

As apparent from the above description, in the ultrasonic probe and the method of manufacturing the same in accordance with exemplary embodiments, the pulsating heat pipe is provided, thereby facilitating the efficient emission of the internal heat generated in the transducer to the outside.

The heat radiation function may be performed in the pulsating heat pipe, whereby the backing layer may perform only the sound absorbing function. As a result, the performance of the backing layer may be optimally designed.

The foregoing exemplary embodiments and advantages are merely exemplary and are not to be construed as limiting. The present teaching can be readily applied to other types of apparatuses. Also, the description of the exemplary embodiments is intended to be illustrative, and not to limit the scope of the claims, and many alternatives, modifications, and variations will be apparent to those skilled in the art.

What is claimed is:

1. An ultrasonic probe comprising:
a transducer array configured to generate ultrasonic waves;
a backing layer that is provided on a rear surface of the transducer array;
a pulsating heat pipe configured to absorb heat generated in the transducer array; and
a heat radiator configured to receive the heat from the pulsating heat pipe to emit the received heat to the outside,
wherein the pulsating heat pipe includes:
a heating portion that is inserted into the backing layer so that a working fluid is heated by the heat generated in the transducer array,
a heat insulating portion configured to transport the heated working fluid, and
a cooling portion configured to contact the heat radiator and cool the working fluid transported through the heat insulating portion,
wherein the backing layer comprises layers containing mutually different sound absorbing materials, and
wherein the pulsating heat pipe is inserted into any one of the layers of the backing layer or any one of respective boundaries between each two of the layers.

2. The ultrasonic probe according to claim 1, wherein the heating portion extends from a first location at one surface of the backing layer to other surface of the backing layer, different from the one surface.

3. The ultrasonic probe according to claim 2, wherein the heating portion is configured to penetrate the backing layer so that a portion of the pulsating heat pipe is configured to be exposed through the other surface of the backing layer, and
an exposed portion of the pulsating heat pipe is connected to the one surface of the backing layer at a second location different from the first location.

4. The ultrasonic probe according to claim 1, wherein the heating portion is inserted into one surface of the backing layer, extends in the backing layer, and is exposed through a same one surface of the backing layer.

5. The ultrasonic probe according to claim 1, wherein a portion of the pulsating heat pipe is exposed through one surface of the backing layer at a first location and is connected to the one surface of the backing layer via the heat radiator at a second location different from the first location, and
the heat radiator extends in the backing layer.

6. The ultrasonic probe according to claim 1, wherein the transducer array includes:
a transducer element configured to vibrate to generate the ultrasonic waves; and
an application specific integrated circuit (ASIC) configured to control a current supplied to the transducer element.

7. The ultrasonic probe according to claim 6, wherein the pulsating heat pipe is configured to transfer heat generated in the ASIC to the heat radiator.

8. The ultrasonic probe according to claim 1, wherein the heat radiator comprises a metal to absorb the heat from the pulsating heat pipe.

9. A method of manufacturing an ultrasonic probe, the method comprising:
providing a transducer array configured to generate ultrasonic waves;
providing a backing layer on a rear surface of the transducer array;
providing a pulsating heat pipe configured to absorb heat generated in the transducer array; and
providing a heat radiator configured to receive the heat from the pulsating heat pipe to be emitted to the outside,
wherein the providing the pulsating heat pipe includes:
inserting a heating portion into the backing layer so that a working fluid is heated by the heat generated in the transducer array,
providing a heat insulating portion through which the heated working fluid is transported, and providing a cooling portion in contact with the heat radiator so that the working fluid transported through the heat insulating portion is cooled, wherein the providing the backing layer includes providing layers containing mutually different sound absorbing materials, and wherein the providing the pulsating heat pipe further includes inserting the pulsating heat pipe into any one of the layers of the backing layer or any one of respective boundaries between each two of the layers.

10. The method according to claim 9, wherein the inserting the heating portion into the backing layer includes extending the heating portion from one surface of the backing layer to other surface thereof so that the heating portion penetrates the backing layer, and the one surface is different from the other surface.

11. The method according to claim 10, wherein the providing the pulsating heat pipe further includes:

extending the cooling portion which contacts the heat radiator so that the cooling portion is connected to the one surface of the backing layer.

12. The method according to claim 9, wherein the inserting the heating portion into the backing layer includes:

inserting the heating portion into one surface of the backing layer so that the heating portion extends in the backing layer and is exposed through a same one surface of the backing layer.

13. The method according to claim 12, wherein the providing the pulsating heat pipe further includes:

extending the cooling portion which contacts the heat radiator so that the cooling portion is connected to the one surface of the backing layer.

14. The method according to claim 9, wherein the providing the transducer array includes:

providing a transducer element configured to vibrate to generate the ultrasonic waves, and providing an application specific integrated circuit (ASIC) configured to control a current supplied to the transducer element.

15. The method according to claim 9, wherein the providing the heat radiator includes:

providing the heat radiator made of a metal so that the heat radiator absorbs heat from the pulsating heat pipe.

* * * * *